(12) United States Patent
Peltier et al.

(10) Patent No.: US 11,191,744 B2
(45) Date of Patent: Dec. 7, 2021

(54) PHARMACEUTICAL ACTIVE INGREDIENT AND USE THEREOF, IN PARTICULAR FOR THE PREVENTION AND TREATMENT OF METABOLIC DISORDERS IN HUMANS AND ANIMALS

(71) Applicants: VALBIOTIS, Perigny (FR); UNIVERSITE CLERMONT AUVERGNE, Clermont Ferrand (FR); UNIVERSITE DE LA ROCHELLE, La Rochelle (FR); CNRS, Paris (FR)

(72) Inventors: Sebastien Peltier, Fouras (FR); Vivien Chavanelle, Clermont-Ferrand (FR); Florian Le Joubioux, Aytre (FR); Pascal Sirvent, Ceyrat (FR); Thierry Maugard, La Jarne (FR)

(73) Assignees: VALBIOTIS, Perigny (FR); UNIVERSITE CLERMONT AUVERGNE, Clermont Ferrand (FR); UNIVERSITE DE LA ROCHELLE, La Rochelle (FR); CNRS, Paris (FR)

( * ) Notice: Subject to any disclaimer, the term of this patent is extended or adjusted under 35 U.S.C. 154(b) by 0 days.

(21) Appl. No.: 16/486,381

(22) PCT Filed: Feb. 13, 2018

(86) PCT No.: PCT/EP2018/053520
§ 371 (c)(1),
(2) Date: Aug. 15, 2019

(87) PCT Pub. No.: WO2018/149812
PCT Pub. Date: Aug. 23, 2018

(65) Prior Publication Data
US 2020/0009101 A1  Jan. 9, 2020

(30) Foreign Application Priority Data
Feb. 16, 2017 (FR) ...................................... 1770144

(51) Int. Cl.
| | | |
|---|---|---|
| *A61K 31/216* | (2006.01) | |
| *A61K 31/7048* | (2006.01) | |
| *A61P 3/00* | (2006.01) | |
| *A61P 3/04* | (2006.01) | |
| *A61P 3/06* | (2006.01) | |
| *A61P 3/10* | (2006.01) | |

(52) U.S. Cl.
CPC ........ *A61K 31/216* (2013.01); *A61K 31/7048* (2013.01); *A61P 3/04* (2018.01); *A61P 3/06* (2018.01); *A61P 3/10* (2018.01)

(58) Field of Classification Search
CPC .............. A61K 31/216; A61K 31/7048; A61K 2300/00; A61P 3/00
See application file for complete search history.

(56) References Cited

U.S. PATENT DOCUMENTS

| | | | |
|---|---|---|---|
| 2007/0009620 A1* | 1/2007 | Aoki ...................... | A61K 36/63 424/769 |
| 2008/0113935 A1* | 5/2008 | Yedgar ................. | A61K 47/544 514/56 |
| 2011/0046212 A1* | 2/2011 | Berti ........................ | A61P 3/10 514/451 |

FOREIGN PATENT DOCUMENTS

WO  2009118380 A1  10/2009

OTHER PUBLICATIONS

Williams et al. (Foye's Principles of Medicinal Chemistry, 5th edition, pp. 50 and 59-61, 2002).*
Jin S. et al., "Chlorogenic Acid Improves Late Diabetes through Adiponectin Receptor Signaling Pathways in db/db Mice", PLOS ONE, Apr. 7, 2015, pp. 1-15, vol. 10, No. 4.
Garambone E. et al., "Possíveis benefícios do ácido clorogênico à saúde—Possible health benefits of chlorogenic acid", Alimentos E Nutrção Araraquara, Jun. 2007, pp. 229-235, vol. 18, No. 2.
Andreadou I. et al., "The Olive Constituent Oleuropein Exhibits Anti-ischemic, Antioxidative, and Hypolipidemic Effects in Anesthetized Rabbits", The Journal of Nutrition, American Society for Nutrition, 2006, pp. 2213-2219, vol. 136, No. 8.

* cited by examiner

*Primary Examiner* — Theodore R. Howell
(74) *Attorney, Agent, or Firm* — Greer, Burns & Crain, Ltd.

(57) ABSTRACT

The invention relates to an active pharmaceutical ingredient consisting exclusively of the combination of (1S,3R,4R,5R)-3-{[(2E)-3-(3,4-)dihydroxyphenyl)-2-propenoyl]oxy}-1,4,5-trihydroxycyclohexanecarboxylic acid and of methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate for use as a drug or veterinary product, particularly in the prevention and/or treatment of pathological disorders of carbohydrate and/or lipid metabolism.

17 Claims, 5 Drawing Sheets

PHARMACEUTICAL ACTIVE INGREDIENT AND USE THEREOF, IN PARTICULAR FOR THE PREVENTION AND TREATMENT OF METABOLIC DISORDERS IN HUMANS AND ANIMALS

CROSS-REFERENCE TO RELATED APPLICATIONS

This application is the U.S. National phase application corresponding to PCT/EP2018/053,520 which was assigned an international filing date of Feb. 13, 2018 and associated with publication WO 2018/149,812 A1 and which claims priority to FR 1770144 filed on Feb. 16, 2017, the disclosures of which are expressly incorporated herein by reference.

TECHNICAL FIELD

This invention relates to an active pharmaceutical ingredient consisting of the combination of two molecules, and its use as a drug, in particular in the prevention and/or treatment of pathological disorders of carbohydrate and/or lipid metabolism.

BACKGROUND

Chronic metabolic disorders and diseases are becoming more common. This is the case of type 2 diabetes, which has become a major medical challenge worldwide (Boyle J P et al., Popul Health Metr 2010; 8. 29). According to the International Diabetes Federation (IDF), the number of people with type 2 diabetes was 415 million in 2015 and will reach 642 million by 2040, an increase of 55% (IDF Diabetes Atlas, 7$^{th}$ edition). In 2015, diabetes caused 5 million deaths, which is to say one death every six seconds, and global health expenditures for this condition were $673 billion.

Type 2 diabetes is characterized by an abnormally high blood sugar concentration and carbohydrate intolerance. The main cause of this chronic hyperglycemia is insulin resistance as well as inadequate secretion in response to a given metabolic state (Beigi F I, N Eng J Med 2012; 366: 1319-27). To combat this pathology, it is mainly necessary to reduce glycemia levels and reduce glycated hemoglobin (HbA$_1$c) to a rate of less than or equal to 7.0% for adults (excluding pregnant women, ADA, Diabetes Care 2015; 38 (1): S33-S40). The vast majority of patients diagnosed are under pharmacological treatment for the rest of their lives (Qaseem A et al., Ann Intern Med 2012; 156:218-31). Furthermore, current therapies are not effective in correcting the causes of type 2 diabetes (Tao H et al., Nat Med 2014; 20 (11):1263-69), in particular insulin resistance and the loss in the ability of the pancreas to secrete insulin with regard to increased glycemia. Thus, most patients become resistant to current treatments (Qaseem A et al., Ann Intern Med 2012; 156:218-31; D Nathan et al., Diabetes Care 2009; 32:193-203). The development of new drugs, particularly those able to better maintain insulin secretion in response to increased glycemia, is a priority in the fight against the development of type 2 diabetes and its complications. By these effects, such drugs would delay, or rather avoid, the implementation of insulin therapy.

In diabetic patients, there is also a significant prevalence of NAFLD ranging from 50 to 70% (Anstee Q et al., Nat Rev Gastroenterol Hepatol 2013; 10:330-44, Targher G et al., Diabetes Care 2007; 30:1212-8, Williamson R et al., Diabetes Care 2011; 34:1139-44). NAFLD or non-alcoholic fatty liver disease includes a spectrum ranging from simple fatty liver disease to non-alcoholic steatohepatitis (NASH) and cirrhosis (Angulo P N Eng J Med 2002; 346:1221-31; Neuschwander-Tetri B et al., Hepatology 2003; 37:1202-19; Adams L et al., Gastroenterology 2005; 129:113-21; Kotronen A et al. J Clin Endocrinol Metab 2007; 92:3490-7). NAFLD is characterized by an excessive intrahepatic accumulation of fat (steatosis), which can be isolated or associated with a non-specific hepatic inflammation. NASH is the progressive form of NAFLD and is defined by the combination of a steatosis in more than 5% of hepatocytes with a lobular inflammation and with hepatocyte injury (balloonization) (Adams L et al., Cmaj 2005; 172:899-905; Kleiner D et al., Hepatology 2005; 41:1313-21; Brunt E Nat Rev Gastroenterol Hepatol 2010; 7:195-203). Simple steatosis affecting between 1 and 5% of hepatocytes is considered to be physiological and is a benign evolution, whereas NASH is defined by hepatocyte damage, inflammation and/or fibrosis which can lead to cirrhosis, liver failure and hepatocellular carcinoma (Vanni E et al Dig liver Dis 2010; 42:320-30).

In addition, patients with type 2 diabetes have a high risk of cardiovascular morbidity and mortality. It is therefore also necessary to take charge of traditional cardiovascular risk factors such as the control of circulating lipids and weight. This need currently incurs the simultaneous taking of several drugs of different therapeutic classes. The combination of drugs can sometimes lead to serious secondary reactions such as, for example, the simultaneous administration of fibrates and statins which increases the risk of myopathy (Denke M J Manag Care Pharm 2003; 9:17-9).

There is therefore an urgent need for drugs whose "multi-target" mechanism of action has advantages in terms of compliance, tolerance and efficiency. Such products would reduce the overall risk of cardio-metabolic diseases and prevent and treat each dysfunction and/or its consequences independently.

SUMMARY

A goal of this invention is to provide an active ingredient responding to these unmet medical needs, which is particularly able to maintain adequate insulin secretion in response to the increase in glycemia during the development of type 2 diabetes.

It is important to note that in the majority of cases, in an adult patient, NAFLD and NASH are associated with insulin resistance and its phenotypic complications, mainly the conditions that are part of the metabolic syndrome: type 2 diabetes, obesity, arterial hypertension, hypercholesterolemia and hypertriglyceridemia (Marchesini G et al., Diabetes 2001; 50:1844-50; Ratziu V et al., J Hepatol 2010; 53:372-84; Neuschwander-Tetri BA and Hepatology 2003; 37:1202-19).

Another objective of this invention is therefore to provide an active ingredient able:
to reduce insulin resistance;
to reduce oxidative stress and inflammation;
to limit the development of adipocytes;
to reduce the level of circulating triglycerides.

To meet these objectives, the invention provides the use of an active pharmaceutical ingredient consisting exclusively of the combination:
of the (1S,3R,4R,5R)-3-{[(2E)-3-(3,4-dihydroxyphenyl)-2-propenoyl]oxy}-1,4,5-trihydroxycyclohexanecarboxylic acid, and of methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate).

Plant extracts containing these molecules have already been described in literature for applications in nutritional products and in pharmaceutical compositions, but surprisingly, the results obtained with the active ingredient according to the invention are different from those which could be obtained with plant extracts containing these two molecules. The active ingredient consists solely of these two molecules that act synergistically, in particular to reduce fasting glycemia, and to limit the loss of the ability of the pancreas to secrete insulin with the increase in glycemia. Advantageously, the active ingredient according to the invention also makes it possible to envisage a later introduction of insulin therapy, which translates for patients into a considerable improvement in the quality of life (delayed or even avoided insulin injections).

Advantageously, such an active ingredient thus makes it possible to limit or even avoid insulin resistance, an important mechanism for the development of type 2 diabetes.

In addition, the active ingredient according to the invention is able to act on oxidative stress, inflammation, and on lipid metabolism by decreasing, in particular, the development of adipocytes and serum triglycerides.

Therefore, the invention relates to a pharmaceutical active ingredient consisting exclusively of the combination of (1S,3R,4R,5R)-3-{[(2E)-3-(3,4-dihydroxyphenyl)-2-propenoyl]oxy}-1,4,5-trihydroxycyclohexanecarboxylic acid and methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate, for use as a drug or veterinary product, in particular, for preventing and/or treating pathological disorders of carbohydrate and/or lipid metabolism in humans or animals.

The invention also relates to pharmaceutical compositions comprising an active ingredient consisting exclusively of the combination of (1S,3R,4R,5R)-3-{[(2E)-3-(3,4-dihydroxyphenyl)-2-propenoyl]oxy}-1,4,5-trihydroxycyclohexanecarboxylic acid and methyl (2S,3E,4S)-4-{2-[2-(3,4-dihydroxyphenyl)ethoxy]-2-oxoethyl}-3-ethylidene-2-(βD-glucopyranosyloxy)-3,4-dihydro-2H-pyran-5-carboxylate for this same use.

BRIEF DESCRIPTION OF THE DRAWINGS

The invention is now described in detail with reference to the appended figures which represent.

DETAILED DESCRIPTION

Figure 1:
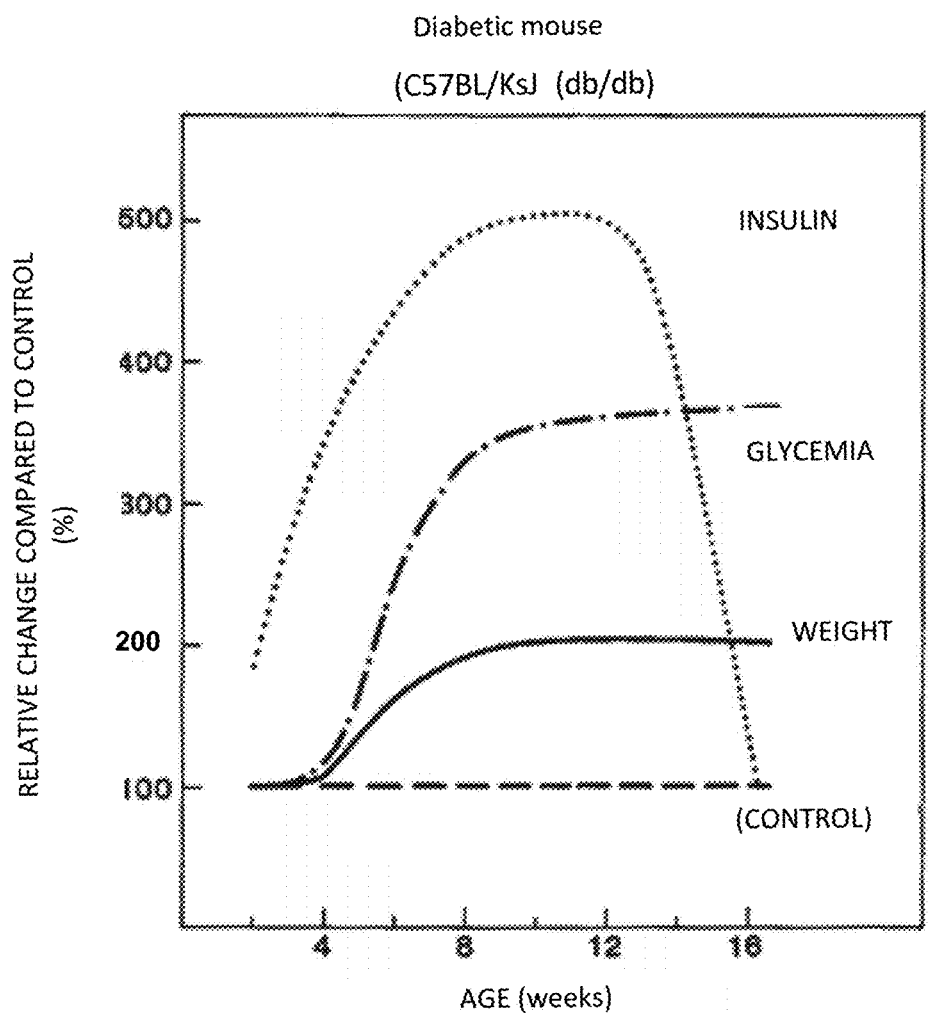
FIG. 1: An illustration of the development of type 2 diabetes in mice.

The invention relates to an active pharmaceutical ingredient consisting exclusively of the combination of (1S,3R,4R,5R)-3-{[(2E)-3-(3,4-dihydroxyphenyl)-2-propenoyl]oxy}-1,4,5-trihydroxycyclohexanecarboxylic acid and methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate for use as a drug or veterinary product.

The (1S,3R,4R,5R)-3-{[(2E)-3-(3,4-dihydroxyphenyl)-2-propenoyl]oxy}-1,4,5-trihydroxycyclohexanecarboxylic acid corresponds to the following formula:

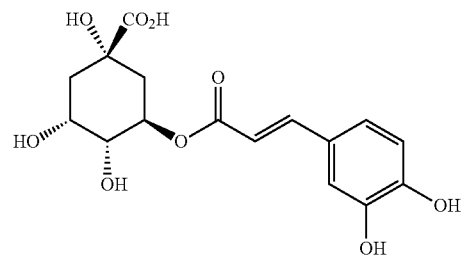 [SMILES: O=C(/C=C/c1ccc(O)c(O)c1)O[C@@H]1C[C@](O)(C(=O)O)C[C@@H](O)[C@H]1O]

It may be referred to as "V63X35" in the examples and tests presented in this application. Methyl (2S,3E,4S)-4-{2-[2-(3,4-hydroxyphenyl)ethoxy]-2-oxoethyl}-3-ethylidene-2-(β-D-glucopyranosyloxy)-3,4-dihydro-2H-pyran-5-carboxylate) corresponds to the following formula:

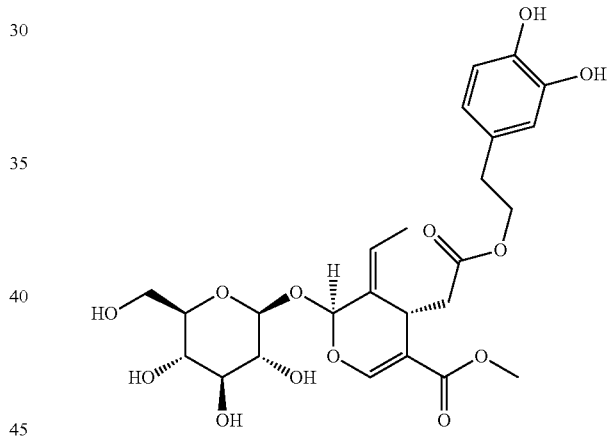

It may be referred to as "V63X54" in the examples and tests presented in this application. These two molecules constituting the active ingredient according to the invention are natural molecules or of chemical and/or biotechnological synthesis. Natural molecules refer to molecules extracted from a vegetable raw material having a purity of between 80% and 100%. The active ingredient consists exclusively of these two molecules and does not contain others except for possible impurities in the case of molecules extracted from vegetable raw material.

Preferentially, the ratio of (1S,3R,4R,5R)-3-{[(2E)-3-(3,4-dihydroxyphenyl)-2-propenoyl]oxy}-1,4,5-trihydroxycyclohexanecarboxylic acid over methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2Hpyran-5-carboxylate by weight is between 1/40 and 1/1, even more preferably between 1/1 and 1/10. Indeed, these ratios make it possible to obtain optimal efficacy for the prevention and/or the treatment of disorders in carbohydrate and/or lipid metabolism, in particular, in the fight against type 2 diabetes.

The active ingredient according to the invention may be in dry form so as to be taken orally, the dry form allowing the production of solid galenics such as tablets or capsules. The active ingredient according to the invention may also be in liquid form for use orally, enterally, parenterally or subcutaneously.

The active ingredient according to the invention can be obtained by any suitable method. It can, in particular, be obtained by simply mixing the two molecules in the desired proportions.

Preferentially, the molecules constituting the active ingredient according to the invention is obtained by a chemical and/or biotechnological synthesis process of the two molecules.

The synthesis of the (1S,3R,4R,5R)-3-{[(2E)-3-(3,4-dihydroxyphenyl)-2-propenoyl]oxy}-1,4,5-trihydroxycyclohexanecarboxylic acid can be achieved by chemical and/or enzymatic coupling of the (2E)-3-(3,4-dihydroxyphenyl) acrylate with the (1S,3R,4S,5R)-1,3,4,5-tetrahydroxycyclohexanecarboxylic acid. The esterification reaction can preferably be carried out in a so-called unconventional medium with a lipase-type enzyme catalyst.

The synthesis of the methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate can be achieved by chemical and/or enzymatic coupling of the 4-(2-hydroxyethyl)-1,2-benzenediol with the [(2S,3S,4S)-3-formyl-5-(methoxycarbonyl)-2-methyl-3,4-dihydro-2H-pyran-4-yl] acetic acid, previously glucosylated. The esterification reaction and glucosylation can preferably be performed in a so-called unconventional medium by enzyme catalysts, a lipase and a β-D-glucosidase respectively.

Preferentially, the active ingredient according to the invention is used in a pharmaceutical composition.

The invention therefore also relates to a pharmaceutical composition comprising at least one active ingredient as described above, for use as a drug or veterinary product. Such a composition may be in solid or liquid form, depending on the mode and the form of administration chosen for the active ingredient.

The active ingredient according to the invention is preferably between 0.05% (for example a compressed form with excipients) and 100% by weight of dry matter of the final composition (excluding carrier, for example an active ingredient amounting to 100% of the composition within a capsule).

The wet weight of the active ingredient as a percentage of the final composition depends on the nature of the excipients used.

The composition, when it is in dry form or in a dry form to be reconstituted in water, in addition to the active ingredient according to the invention, may optionally comprise at least one excipient adapted to this form, chosen from, by way of example but not limited to: stearic acid, corn starch, microcrystalline cellulose, citral, croscarmellose sodium salt, crospovidone, iron oxide yellow, gelatin, geraniol, xanthan gum, hydroxypropyl cellulose, hypromellose, indigotin, macrogol 400, macrogol 8000, magnesium stearate, maltodextrin, opadry clear, povidone K 30, propylene glycol, colloidal anhydrous silica, sodium carboxymethyl starch, sodium benzoate, titanium dioxide.

The composition, in addition to the active ingredient according to the invention, when it is in liquid form, may optionally comprise at least one excipient adapted to this form, chosen, by way of example but not limited to: benzyl alcohol, carmellose sodium, cetylpyridinium chloride, water for injection (WFI), glycerol, metacresol, phenol, monosodium phosphate dihydrate, disodium phosphate dihydrate, disodium phosphate dodecahydrate, propylene glycol, polysorbate 80, *Escherichia coli* proteins, sodium chloride, sodium hydroxide, zinc chloride.

The active pharmaceutical ingredient and the composition according to the invention may in particular be used in the prevention and/or treatment of pathological disorders of carbohydrate and/or lipid metabolism in humans or animals.

Pathological metabolism disorders within the meaning of the invention refer to any disruption promoting and/or aggravating and/or at the origin of metabolic pathologies. Metabolic conditions form a pathological environment grouping multifactorial disorders more or less linked by origin, metabolic targets or common mechanisms.

Carbohydrate metabolism imbalance within the meaning of the invention refers to any disruption of the cellular metabolism of carbohydrates that can lead to and/or promote and/or aggravate pathologies. For example, type 2 diabetes is associated with an imbalance of carbohydrate metabolism including, in particular, increased hepatic glucose production. Lipid metabolism imbalance within the meaning of the invention refers to be a modification of the cellular metabolism of lipids which can lead to and/or favor and/or aggravate pathologies. For example, NAFLD is associated with a lipid metabolism imbalance with, in particular, excessive intrahepatic accumulation of fats.

The active ingredient and the composition according to the invention are especially effective in the prevention and/or treatment of at least one disease chosen from:
  type 2 diabetes, by maintaining adequate insulin secretion in response to increased glycemia levels during disease development;
  non-alcoholic fatty liver diseases, in particular NAFLD and NASH, by acting on insulin resistance, oxidative stress and inflammation;
  dyslipidemia, in particular by decreasing serum triglycerides;
  obesity by decreasing the development of adipocytes;
  metabolic syndrome;
  cardiovascular pathologies, in particular, cardiovascular pathologies resulting from complications of type 2 diabetes and/or NAFLD or NASH and/or dyslipidemia and/or obesity and/or a metabolic syndrome, in particular, those selected from among coronary heart diseases, cerebrovascular diseases, peripheral arterial diseases and deep vein thromboses. For these effects, the two molecules constituting the active ingredient according to the invention act in synergy.

When administered orally to humans, especially in patients suffering from type 2 diabetes, the active ingredient according to the invention is preferably administered at a rate of between 5 and 5,000 mg/day, even more preferably between 100 and 3,000 mg/day. The enteral, parenteral or intraperitoneal dose is preferably lesser by at least a factor of 5.

When administered orally to dogs or cats, in particular in dogs or cats suffering from type 2 diabetes, the active ingredient according to the invention is preferably administered in an amount of between 1 and 5,000 mg/day, even more preferably between 10 and 2,000 mg/day. The enteral, parenteral or intraperitoneal dose is preferably lesser by at least a factor of 5.

Figure 5:
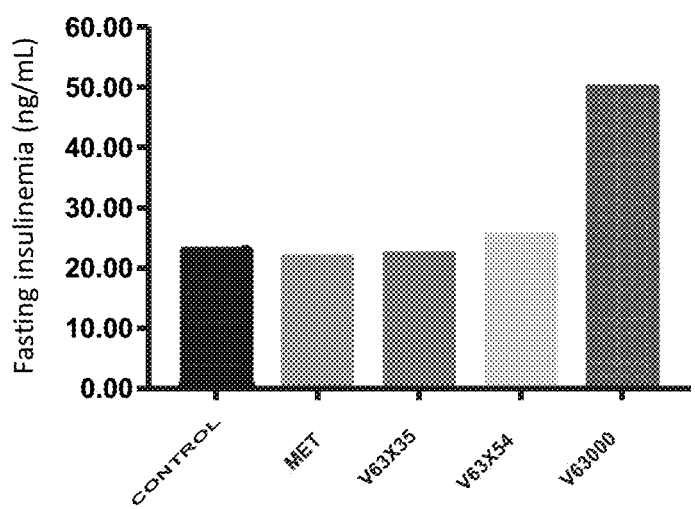
FIG. 5: The results of the test in section II, relating to fasting insulinemia after 6 weeks of treatment (median values), these results corresponding to the results in Table 3.

Advantageously, the active ingredient and composition according to the invention allow to decrease glycemia, to maintain adequate insulin secretion in response to the increase in glycemia during the development of type 2 diabetes, to improve insulin sensitivity, to decrease inflammation and oxidative stress, to decrease serum triglycerides, and to regulate beneficial development of adipocytes. In particular, the effects of the active ingredient according to the invention are greater than those of the reference drug in the treatment of type 2 diabetes, metformin, on insulin metabolism (FIG. 5).

Moreover, the possible oral intake of the active ingredient and the composition according to the invention is a definite advantage over many antidiabetic molecules only administrable by injection (examples: dulaglutide, liraglutide, insulin glargine/lixisenatide combo).

The invention is here illustrated by examples of active ingredients and compositions, as well as by test results demonstrating the effectiveness of the invention, these examples and tests being not limiting.

EXAMPLES

Example 1

Example of Active Ingredient According to the Invention

The active ingredient according to the invention of Example 1 is made up of the combination of (1S,3R,4R5R)-3-{[(2E)-3-(3,4-dihydroxyphenyl)-2-propenoyl]oxy}-1,4,5-trihydroxycyclohexanecarboxylic acid and of methyl (2S,3E,4S)-4-{2-[2-(3,4-dihydroxyphenyl)ethoxy]-2-oxoethyl}-3-ethylidene-2-($\beta$-D-glucopyranosyloxy)-3,4-dihydro-2H-pyran-5-carboxylate in a ratio of 1/4.6 in dry form.

The synthesis of (1S,3R,4R,5R)-3-{[(2E)-3-(3,4-dihydroxyphenyl)-2-propenoyl]oxy})-1,4,5-trihydroxycyclohexanecarboxylic acid was achieved by the coupling of (2E)-3-(3,4-dihydroxyphenyl) acrylate with the (1S,3R,4S,5R)-1,3,4,5-tetrahydroxycyclohexanecarboxylic acid. This esterification reaction is preferably performed by a chemical and/or biotechnological coupling process of the two molecules. Preferentially, the coupling has been achieved in a so-called unconventional medium by an enzymatic lipase-type catalyst. It is preferentially the lipase B of *Candida antarctica*, at a concentration of 20 g/L, to catalyze in 12 hours the coupling of 150 mM of (2E)-3-(3,4-dihydroxyphenyl)acrylate with 150 mM of (1S,3R,4S,5R)-1,3,4,5-tetrahydroxycyclohexanecarboxylic acid in a 40/60 (v/v) mixture of 2-methylbutan-2-ol/n-hexane at 55° C.

The synthesis of methyl (2S,3E,4S)-4-{2-[2-(3,4-dihydroxyphenyl)ethoxy]-2-oxoethyl)}-3-ethylidene-2-($\beta$-D-glucopyranosyloxy)-3,4-dihydro-2H-pyran-5-carboxylate was achieved by the chemical and/or enzymatic coupling of the 4-(2-hydroxyethyl)-1,2-benzenediol with the [(2S,3S,4S)-3-formyl-5-(methoxycarbonyl)-2-methyl-3,4-dihydro-2H-pyran-4-yl] acetic acid, previously glucosylated. The esterification and glycosylation reaction was achieved in a so-called unconventional medium by enzyme catalysts, a lipase and a $\beta$-D-glycosidase respectively.

Preferentially, lipase B of *Candida antarctica* is used, at a concentration of 20 g/L, to catalyze in 24 hours the coupling of 150 mM of 4-(2-hydroxyethyl)-1,2-benzenediol with 75 mM of the [(2S,3S,4S)-3-formyl-5-(methoxycarbonyl)-2-methyl-3,4-dihydro-2H-pyran-4-yl] acetic acid, previously glucosylated, in a 90/10 (v/v) mixture of 2-methylbutan-2-ol/n-hexane at 55° C. Preferentially, the glucosidase of *Sclerotinia sclerotiorum* is used, at a concentration of 30 U/ml, to catalyze the glucosylation in 10 hours of 50 mM of [(2S,3S,4S)-3-formyl-5-(methoxycarbonyl)-2-methyl-3,4-dihydro-2H-pyran-4-yl] acetic, with 100 mM of pNP-$\beta$-D-glucopyranoside in a 30/70 (v/v) DMSO/acetone mixture at 40° C.

Example 2

Example of a Composition According to the Invention

The composition according to the invention of Example 2 comprises per daily dose 100 mg of (1S,3R,4R,5R)-3-{[(2E)-3-(3,4-dihydroxyphenyl)-2-propenoyl]oxy}-1,4,5-trihydroxycyclohexanecarboxylic acid and 460 mg of methyl (2S,3E,4S)-4-{2-[2-(3,4-dihydroxyphenyl)ethoxy)]-2-oxoethyl}-3-ethylidene-2-($\beta$-D-glucopyranosyloxy)-3,4-dihydro-2H-pyran-5-carboxylate in dry form.

The composition according to the invention is in the form of scored white tablets of 1200 mg. It includes the following excipients: hypromellose, magnesium stearate, povidone K 30. The excipients therefore represent 640 mg. The active ingredient according to the invention represents 53.3% of the total weight of the tablet, the excipients 46.7%. The tablet is made according to methods known to those skilled in the art.

Example 3

Example of a Composition According to the Invention

The composition according to the invention comprises, per daily dose, 1 mg of the (1S,3R,4R,5R)-3-{[(2E)-3-(3,4-dihydroxyphenyl)-2-propenoyl]oxy}-1,4,5-trihydroxycyclohexanecarboxylic acid and 6 mg of methyl (2S,3E,4S)-4-{2-[2-(3,4-dihydroxyphenyl)ethoxy]-2-oxoethyl}-3-ethylidene-2-($\beta$-D-glucopyranosyloxy)-3,4-dihydro-2H-pyran-5-carboxylate in liquid form. The composition according to the invention is in injectable form having as excipients: benzyl alcohol, sodium carmellose, cetylpyridinium chloride, WFI, polysorbate 80, sodium chloride. The injectable solution is made according to methods known to those skilled in the art.

In Vivo Evaluation of the Effectiveness of the Composition

In vivo experiments on mice were performed to demonstrate the effects of the active ingredient according to the invention, in particular on fasting glycemia and insulin secretory capacity in response to a chronic increase in fasting glycemia. The composition was also compared to metformin, one of the main pharmaceutical molecules prescribed for the treatment of type 2 diabetes.

Experiments were performed on db/db mice, a model mimicking the characteristics of type 2 diabetes in humans (Roesler W J et al., Mol Cell Biochem 1990; 92(2):99-106). These mice are insulin-resistant, hypertriglyceridemic, and glucose intolerant. They very quickly develop pre-diabetes, a type 2 diabetes and then NASH.

FIG. 1 illustrates the evolution of insulinemia and glycemia (glucose) over time in this model (Joost H G et al., Animal Models in Diabetes Research, Humana Press). As for humans, the rise in glycemia is initially accompanied by an increase in insulinemia (associated with insulin resistance), evidence of a pancreas still able to secrete insulin, then a decrease, reflecting functional degeneration of the pancreas, and thus progression of type 2 diabetes with the need for insulin therapy (Kobayashi K et al., Metabolism: Clinical and experimental 2,000; 49:22-31 Tao H et al Nat Med 2014; 20(11):1263-1269).

The experimental time for the trial was 6 weeks with a 1 week run-in followed by 6 weeks of treatment. The male mice were 6 weeks old at the start of treatment. The (1S,3R,4R,5R)-3-{[(2E)-3-(3,4-dihydroxyphenyl)-2-propenoyl]oxy}-1,4,5-trihydroxycyclohexanecarboxylic acid alone, the methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate alone, and the mixture of these two molecules in a ratio of 1/4.65 have been tested and compared with metformin. These compositions were directly integrated into the diet of rodents, thus ensuring large-scale use, with injections, for example, intravenous, being limited to a small number given their mode of administration.

After randomization by weight and fasting glycemia, the animals were divided into the following groups:

Control (n=15): CONTROL;
Metformin (n=12, 0.2% of the diet): MET;
(1S,3R,4R,5R)-3-{[(2E)-3-(3,4-dihydroxyphenyl)-2-propenoyl]oxy}-1,4,5-trihydroxycyclohexanecarboxylic acid (n=12, 0.026% of the diet): V63X35;
The methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate (n=11, 0.12% of diet): V63X54;
The (1S,3R,4R,5R)-3-{[(2E)-3-(3,4-dihydroxyphenyl)-2-propenoyl]oxy}-1,4,5-trihydroxycyclohexanecarboxylic acid+methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate (n=11, respectively 0.026% and 0.12% of the feed): V63,000.

Mice were fed ad libitum and had free access to water. They were also placed in individual cages. Food intake was measured weekly, except at the end of treatment (week 6), because of the different assessments made.

Experimental evaluations performed on an empty stomach (6 h) after 6 weeks of treatment were in particular concerned with:

The measurement of weight;
Measuring glycemia;
Measuring of insulinemia;
Measuring of serum triglycerides.

Figure 2:
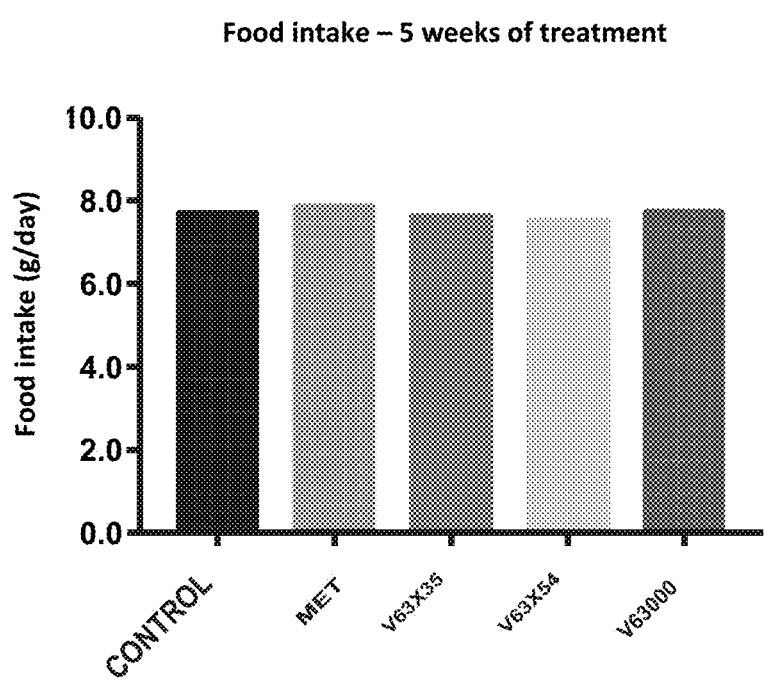
FIG. 2: The results of the test presented in point II, relating to food intake after 5 weeks of treatment (average values), these results corresponding to the results in Table 1.

The results on the measurement of food intake are presented in Table 1 and FIG. 2.

TABLE 1

Food intake after 6 weeks of treatment

| CONTROL | MET | V63X35 | V63X54 | V63000 |
|---|---|---|---|---|
| 7.7 ± 0.5 | 7.9 ± 0.5 | 7.6 ± 0.6 | 7.5 ± 0.5 | 7.7 ± 0.3 |

Results expressed in g/day; mean values ± SEM (standard error of mean).

Table 1. Food Intake After 6 Weeks of Treatment

It is noted that no composition has induced a change in food intake. The results obtained are therefore independent of food intake. According to the Reagan-Show S et al. method. (FASEB J 2008; 2(3):659-61), the equivalent human dose of the combination of molecules ingested by rodents was 19.4 mg/kg body weight per day.

Figure 3:
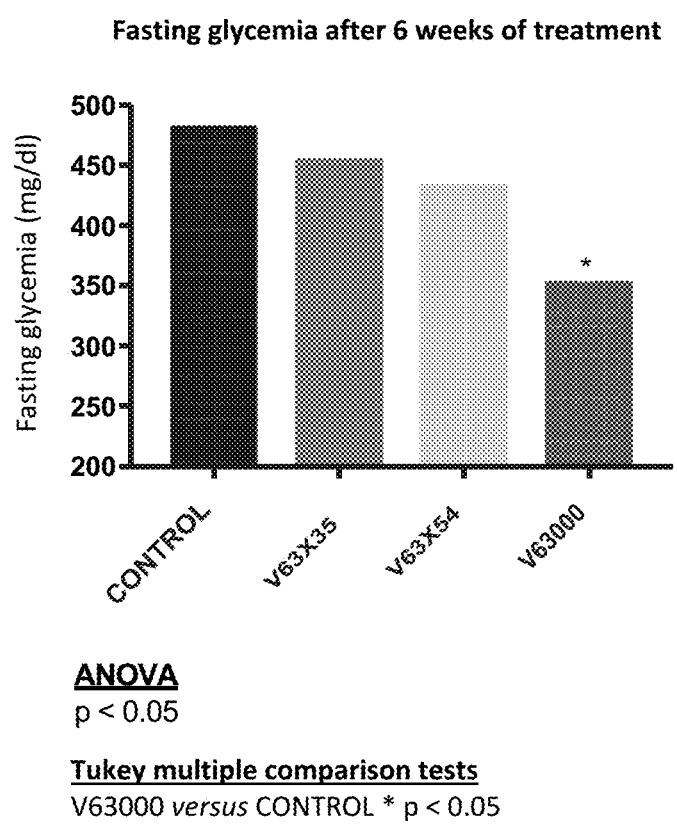
FIG. 3: The results of the test in point II, relating to fasting glycemia (mean values) after 6 weeks of treatment, these results corresponding to the results in Table 2.

The results of the glycemia measurement are shown in Table 2 and FIG. 3.

TABLE 2

Fasting glycemia after 6 weeks of treatment

| CONTROL | MET | V63X35 | V63X54 | V63000 |
|---|---|---|---|---|
| 481 ± 31 | 454 ± 34 | 454 ± 34 | 432 ± 27 | 355 ± 31 |

Results expressed in mg/dL; mean values ± SEM.

Table 2. Fasting Glycemia After 6 Weeks of Treatment

These results show that after 6 weeks of treatment, no effect was observed with the (1S,3R,4R,5R)-3-{[(2E)-3-(3,4-dihydroxyphenyl)-2-propenoyl]oxy}-1,4,5-trihydroxycyclohexanecarboxylic acid alone (V63X35 group) and the methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2Hpyran-5-carboxylate alone (V63X54 group). Only the combination of the two molecules (V63,000) induced a decrease in fasting glycemia (−26.2%, ANOVA p <0.05, multiple Tukey comparison tests: V63,000 versus CONTROL, p<0.05). Metformin had no effect on this parameter (CONTROL, 481 mg/dL versus MET, 454 mg/dL, p=0.56).

The synergistic effect on fasting glycemia was evaluated according to the Colby SR method described in "Calculation of the synergistic and antagonistic responses of herbicide combinations" *Weeds*, 1967, 15:20-22. A factor>1 indicates the existence of a synergistic effect. A factor<1 indicates the existence of an antagonist.

The calculations carried out were:

Expected Efficiency Ratio=$V63X35+V63X54-(V63X35*V63X54/100)$

Synergistic Factor (FS)=(1*Efficacy Rate Observed (%, V63,000))/Expected Efficacy Rate (%)

V63X35 represents the percent change in glycemia for the V63X35 treated group compared to the CONTROL group.

V63X54 represents the percent change in glycemia for the V63X54 group compared to the CONTROL group.

The observed efficacy rate represents the % change in fasting glycemia in the V63,000 group compared to the CONTROL group.

Figure 4:
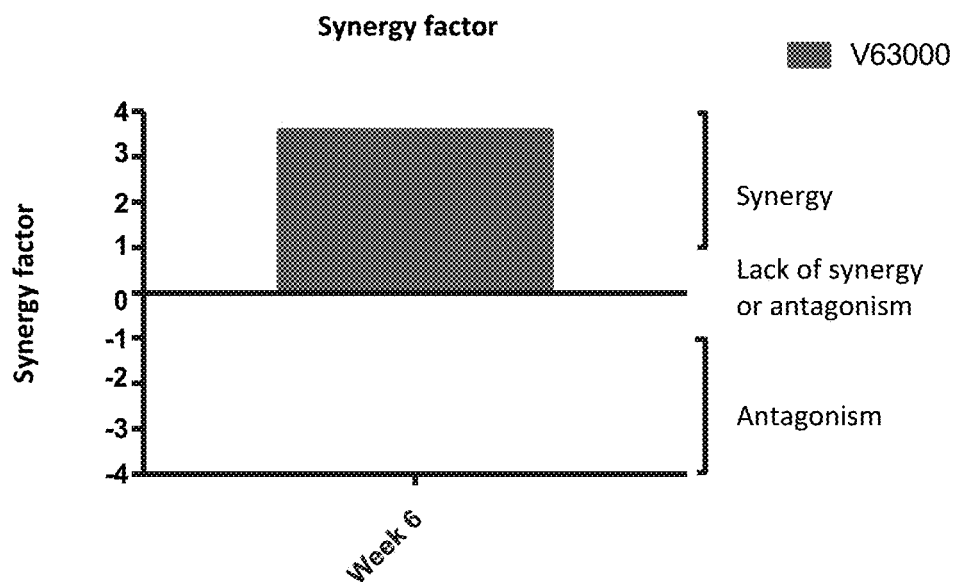
FIG. 4: The results of the test presented in point II, relating to the synergistic factor after 6 weeks of treatment.

The result, shown in FIG. 4, shows a synergistic effect of the combination with an FS=3.58. In conclusion, only the V63,000 combination had an effect on fasting glycemia. This is a synergistic effect, V63X35 and V63X54 having no effect on this parameter. Moreover, the effect of the composition according to the invention is greater than that of metformin, and this despite a lower dose (MET, 0.2% versus V63,000 0.14% of the diet). The absence of effect of metformin on this model has already been reported, as evidenced by the work of Ohno T et al. (metformin 300 mg/kg/day, PLoSONE 2015; 10(4):e0124081). Indeed, metformin appears to be less effective, if not ineffective, in animals with inadequate insulin secretion (GLUCOPHAGE®, metformin, product monograph 2009, Sanofi-Aventis, Canada). In other words, metformin would become ineffective in an advanced state of type 2 diabetes, characterized inter alia by an impairment of the insulin secretory function of the pancreas. Fasting insulin results are shown in Table 3 and FIG. 5 which illustrate the median fasting insulinemia after 6 weeks of treatment in the different groups.

TABLE 3

| Median values of insulinemia after 6 weeks of treatment | | | | |
|---|---|---|---|---|
| CONTROL | MET | V63X35 | V63X54 | V63000 |
| 23.03 | 21.89 | 22.39 | 25.44 | 49.97 |

Results expressed in ng/mL.

Table 3. Median Values of Insulinemia After 6 Weeks of Treatment

It is found that all the median values are identical except for the median value of the V63,000 group which is 216% higher than that of the CONTROL (CONTROL, 23.03 ng/mL versus ACHOLE 49.97 ng/mL) group. These results also demonstrate a synergistic effect of the combination of molecules, with no difference being observed between the median values of the CONTROL, V63X35 and V63X54 groups.

Maintaining adequate insulin secretion in response to a chronic increase in glycemia is a major medical issue for the treatment of type 2 diabetes and its complications. The increase in the median value in the V63,000 group demonstrates a better insulin level in response to the increase in glycemia. Referring to FIG. 1, the active ingredient according to the invention shifts the evolution curve of insulinemia to the right, translating a real efficacy for the treatment or prevention of type 2 diabetes, particularly when in an advanced stage. These results make it possible to imagine a decline in insulin therapy in patients with type 2 diabetes, or even its occurrence.

Figure 6:
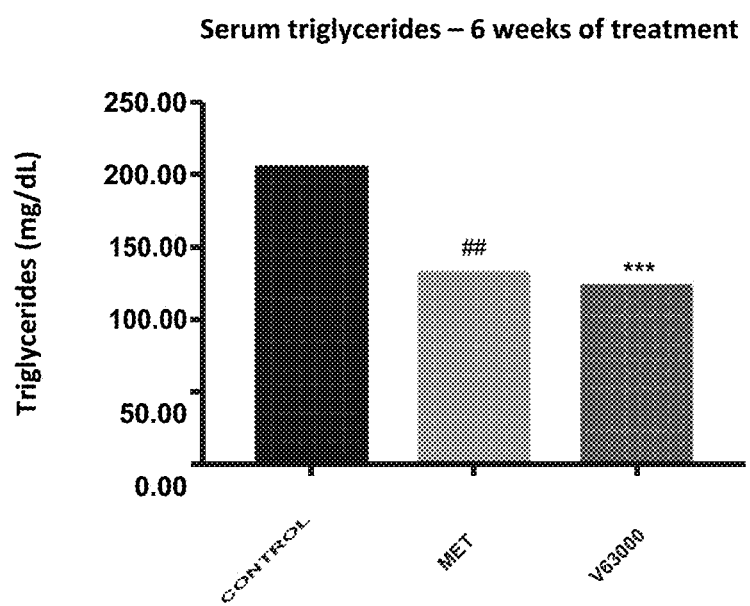
FIG. 6: The results of the test in section II, relating to fasting serum triglycerides after 6 weeks of treatment (mean values), these results corresponding to the results in Table 4.

Finally, the results obtained on blood triglycerides are presented in Table 4 and in FIG. 6.

TABLE 4

| Serum triglycerides after 6 weeks of treatment | | |
|---|---|---|
| CONTROL | MET | V63000 |
| 205.4 ± 17.8 | 132.6 ± 7.4 | 122.8 ± 14.0 |

Results expressed in mg/dL; mean values ± SEM.

Table 4. Serum Triglycerides After 6 Weeks of Treatment

These results show that the metformin and the active ingredient according to the invention reduce blood triglyceride levels by 35.6% and 40.4%, respectively.

The effect of metformin on circulating triglycerides is conventionally described in the various instructions for use of drugs incorporating this molecule. The active ingredient according to the invention also has a favorable effect on the metabolism of lipids thus making it possible to exert a total action on cardiovascular risk.

The invention claimed is:

1. A pharmaceutical composition in the form of a tablet, capsule, gel capsule, powder, sachet, ampoule, solution for dropper or injectable solution, the pharmaceutical composition consisting essentially of a pharmaceutical active ingredient consisting of two compounds, a first compound and a second compound: wherein
the first compound is (1S,3R,4R,5R)-3-{[(2E)-3-(3,4-dihydroxyphenyl)-2-propenoyl]oxy}-1,4,5-trihydroxycyclohexanecarboxylic acid, and wherein
the second compound is methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate,
for use as a drug or veterinary product;
wherein the capsule or the gel capsule increases the bioavailability of the pharmaceutical active ingredient;
wherein the powder, sachet, the ampoule, the solution for dropper or the injectable solution includes at least one excipient other than water.

2. The pharmaceutical composition of claim 1, wherein the active ingredient is in an amount effective for treating at least one disease selected from among type 2 diabetes, non-alcoholic fatty liver diseases, cardiovascular pathologies, dyslipidemia, obesity and metabolic syndrome.

3. The pharmaceutical composition of claim 2, characterized in that the cardiovascular pathologies are selected from among coronary heart disease, cerebrovascular diseases, peripheral arterial diseases and deep vein thromboses.

4. The pharmaceutical composition for use according to claim 2, characterized in that the non-alcoholic fatty liver disease is non-alcoholic fatty liver disease.

5. The pharmaceutical composition of claim 1, characterized in that a ratio of (1S,3R,4R,5R)-3-{[(2E)-3-(3,4-dihydroxyphenyl)-2-propenoyl]oxy}-1,4,5-trihydroxycyclohexanecarboxylic acid to methyl(2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate by weight is in the range from 1:40 to 1:1.

6. The pharmaceutical composition of claim 1, characterized in that it is in liquid form.

7. The pharmaceutical composition of claim 1, wherein the pharmaceutical active ingredient is formulated for administration orally, enterally, parenterally or subcutaneously.

8. The pharmaceutical composition for use according to claim 1, characterized in that it comprises between 0.5 and 100% of the pharmaceutical active ingredient by weight.

9. A method for preventing and/or treating at least one disease selected from among type 2 diabetes, non-alcoholic fatty liver diseases, cardiovascular pathologies, dyslipidemia, obesity and metabolic syndrome, wherein the method comprises administering to a mammal in need of the prevention and/or treatment a drug or veterinary product comprising the pharmaceutical active ingredient of claim 1.

10. The method of claim 9, characterized in that the cardiovascular pathologies are selected from among coronary heart disease, cerebrovascular diseases, peripheral arterial diseases and deep vein thromboses.

11. The method of claim 9, characterized in that the non-alcoholic fatty liver disease is non-alcoholic fatty liver disease.

12. The method of claim 9, wherein the pharmaceutical active ingredient has the ratio of (1S,3R,4R,5R)-3-{[(2E)-3-(3,4-dihydroxyphenyl)-2-propenoyl]oxy}-1,4,5-trihydroxycyclohexanecarboxylic acid over methyl(2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate by weight between 1/40 and 1/1.

13. The method of claim 9, wherein the pharmaceutical active ingredient is further characterized in that the molecules of (1S,3R,4R,5R)-3-{[(2E)-3-(3,4-dihydroxyphenyl)-2-propenoyl]oxy}-1,4,5-trihydroxycyclohexanecarboxylic acid and of (1S,3R,4R,5R)-3-{[(2E)-3-(3,4-dihydroxyphenyl)-2-propenoyl]oxy}-1,4,5-trihydroxycyclohexanecarboxylic acid, and of methyl (2S,3E,4S)-4-{2-[2-(3,4-dihydroxyphenyl)ethoxy]-2-oxoethyl}-3-ethylidene-2-(β-D-glucopyranosyloxy)-3,4-dihydro-2H-pyran-5-carboxylate are natural or synthetic molecules by a chemical and/or biotechnological process.

14. The method of claim 9, wherein the drug or veterinary product is administered orally, enterally, parenterally or subcutaneously.

15. The method of claim 9, wherein the drug or veterinary product is a pharmaceutical composition.

16. The method of claim 9, wherein the drug or veterinary product is in the form of tablets, capsules, gel capsules, powder, sachets, ampoules, solution for dropper or injectable solution.

17. The method of claim 9, wherein the drug or veterinary product comprises between 0.5 and 100% of the pharmaceutical active ingredient by weight of dry matter.

* * * * *